(12) United States Patent
Steinmüller

(10) Patent No.: US 8,220,927 B2
(45) Date of Patent: Jul. 17, 2012

(54) METHOD OF DETERMINING A CONTACT LENS

(75) Inventor: Andreas Steinmüller, Wettenberg (DE)

(73) Assignee: Oculus Optikgeräte GmbH, Wetzler-Dutenhofen (DE)

( * ) Notice: Subject to any disclaimer, the term of this patent is extended or adjusted under 35 U.S.C. 154(b) by 1 day.

(21) Appl. No.: 12/792,255

(22) Filed: Jun. 2, 2010

(65) Prior Publication Data

US 2010/0302509 A1 Dec. 2, 2010

(30) Foreign Application Priority Data

Jun. 2, 2009 (DE) .......................... 10 2009 023 462

(51) Int. Cl.
*A61B 7/02* (2006.01)
*A61B 3/00* (2006.01)
(52) U.S. Cl. .......................... 351/212; 351/203; 351/219
(58) Field of Classification Search .................. 351/200, 351/203, 205, 212, 214, 219, 222, 246
See application file for complete search history.

(56) References Cited

U.S. PATENT DOCUMENTS

| | | | |
|---|---|---|---|
| 3,108,523 | A | 10/1963 | Nuchman et al. |
| 4,878,750 | A | 11/1989 | Sekiguchi |
| 5,414,478 | A | 5/1995 | van Gelderen |
| RE37,196 | E * | 5/2001 | van Gelderen ............... 351/212 |
| 6,379,008 | B1 | 4/2002 | Chateau et al. |
| 7,708,406 | B2 | 5/2010 | Koest |
| 2002/0035485 | A1 * | 3/2002 | Mita et al. ........................ 705/2 |
| 2004/0246440 | A1 | 12/2004 | Andino et al. |

FOREIGN PATENT DOCUMENTS

EP 1 844 704 A1 10/2007

OTHER PUBLICATIONS

"Optometer," thefreedictionary.com, http://medical-dictionary.thefreedictionary.com/p/autorefractometer, printed Jun. 1, 2010.
Stedman's Medical Dictionary, 1995, p. 915.
Beam, J., "What is a Keratometer?" www.wisegeek.com/what-is-a-keratometer.htm, printed Aug. 13, 2010.
"Scheimpflug Principle," http://en.wikipedia.org/wiki/Scheimpflug_principle, printed Aug. 4, 2010, last modified Jun. 17, 2010.
Office Action issued in corresponding European patent application No. 10164555.4 on Jun. 14, 2011.

* cited by examiner

*Primary Examiner* — Joseph P Martinez
*Assistant Examiner* — Brandi Thomas
(74) *Attorney, Agent, or Firm* — Griffin & Szipl, P.C.

(57) ABSTRACT

The invention relates to a method of determining and selecting a contact lens with an opthalmological device for examining the eyes, the opthalmological device comprising a keratometer and an autorefractometer as well as a data processor, whereby a refractive power of an eye and a topography of a cornea are determined, whereby refraction data describing a refraction of an eye to be examined are obtained, whereby topographic data describing the topography of the cornea of the eye are obtained, and whereby, by using the obtained refraction and topography data, contact lens data are calculated and a contact lens is selected from a database of the opthalmological device. In accordance with an apparatus embodiment of the invention, an opthalmological device for carrying out the method is also described.

16 Claims, 2 Drawing Sheets

```
Patient:         Demo Daniel
Date of birth:   23.10.1973
Age:             35

Date:       28.05.2009
Time:       16:27:26
Eye:        Left
QF:         100%

Refraction
    HSA = 12 mm
    S        C        A
    +0.66  +0.19  107°
    +0.68  +0.14  113°
    +0.62  +0.16  115°
    +0.65  +0.16  111°

Pachymetry
PachyApex          570 μm
Pachy Min:  564 μm
IOD table          Dresden
IOD change  -0.8 mmHg Keratometry
Rh:         0.04 mm @ 11°
Rv:         7.99 mm @ 101°
Astig.      0.2D Soft lens
    Rm           Astig.      Axis    HH
    8.01         0.20        11°    -239

S         C          A      HSA
Obj.  +0.81    -0.16 21°     12.00
Subj. +0.50    -0.25 21°     12.00
CL    +0.50    -0.24 21°     0

Selected lens
Ciba Vision
Air Optix Aqua

Wearing duration: 1 month
Material               Lotrafilco B
Dk/t                   103.5

From     To          Stage
S   -8.00   +6.00  0.25

S         C          A      ADD
    +0.50   -0.00

Basic curve:    Diameter:
    8.6 mm          14.2 mm
```

FIG. 1

METHOD OF DETERMINING A CONTACT LENS

This application claims priority from German Patent Application No. 10 2009 023 462.4, filed Jun. 2, 2009, the entire disclosure of which is incorporated herein by reference.

FIELD OF THE INVENTION

The invention relates to a method of determining and selecting a contact lens with an opthalmological device for examining the eyes comprising a keratometer and an autorefractometer as well as means of dataprocessing, whereby a refractive power of an eye and a topography of a cornea are determined, whereby refraction data describing a refraction of an eye to be examined are obtained, whereby topographic data describing the topography of the cornea of the eye are obtained. The invention also relates to an opthalmological device for implementing the method.

BACKGROUND OF THE INVENTION

In order to determine and select a contact lens, more particularly a soft contact lens, it is necessary to determine a refractive power of an eye to which the contact lens is to be adapted, and the topography of a cornea of the eye. On the basis of this data a suitable contact lens from a manufacturer must then be selected. For this, relatively extensive calculations are necessary, which vary depending on the manufacturer, as the manufacturers regularly envisage adaptation regulations that differ from one another. In addition, a diameter of a contact lens must be coordinated to the diameter of the cornea. As the manufacturers provide a series of contact lenses that differ so much in terms of their technical data and/or dimensions, that not all determined measurements can be covered, an iterative procedure is necessary for selecting a contact lens. This means that after the calculation and preselection of suitable contact lenses by an examining person, a series of contact lenses are adapted to the patient, whereby a suitable contact lens is selected on the basis of the subjective visual impression of the patient. A particular drawback here is the fact that the examining person must be relatively well trained in the calculation and/or selection of contact lenses and that the process of calculating and selecting the suitable contact lens takes up a comparatively great amount of time.

The aim of the present invention is, therefore, to propose a method and/or an opthalmological device that simplifies the calculation and adaptation of a contact lens.

SUMMARY OF THE INVENTION

This aim is achieved by a method with the features of a first method embodiment and an opthalmological device with the features of a first apparatus embodiment.

In the method according to the invention for determining and selecting a contact lens with an opthalmological device for examination of the eye, which comprises a keratometer and an autorefractometer, as well as means of dataprocessing, a refractive power of an eye and a topography of a cornea are determined, where refraction data describing refraction of a eye to be examined are obtained, whereby topographic data describing a topography of a cornea are obtained, whereby by means of the obtained refraction and topography data contact lenses are calculated and a contact lens is selected from a database of the device.

This achieves the advantage that the opthalmological device carries out the calculation of the contact lens and selects the suitable contact lens from a database with contact lens data. As the suitable contact lens can be relatively precisely determined in this way, neither complicated calculation by the examining person, nor laborious series of tests with various contact lenses on a patient are necessary.

A comparison of the calculated contact lens data with contact lens data stored in the database can advantageously carried out. Thus, from the objective measuring data a required specified contact lens can be calculated, whereby with this data an actual contact lens is selected in the database present in the device, which appears to be most suitable with regard to the specified contact lens. One criterion for suitability can be maximum conformity of the calculated contact lens data with the contact lens data contained in the database.

In one form of embodiment of the method the measuring data of the calculated contact lens data and the contact lens data of the selected contact lens can be outputted. This can be, for example, in the form of a display on a screen, or in the form of a print-out from a printer, which can be added to the patient's files. An examining person can then also test the plausibility of a selection made by the device.

Carrying out several calculations in various calculation modes can also be envisaged. This means that the obtained data can be subject to several calculations, each based on different modes of calculation. The modes of calculation used can be adapted to or made similar to modes of calculation or contact lens adaptation regulations used by contact lens manufacturers. In this way certain manufacturer-specific deviations can be taken into account at the time of calculation when indicating contact lens data.

More particularly adaptation regulations for contact lens of various manufacturers can be taken into consideration.

Contact lens adaptation regulations can also be taken into account when selecting a contact lens. This means that for subsequent calculations various contact lens adaptation regulations of contact lens manufacturers can if necessary be additionally used for selecting a suitable contact lens.

Measuring data can advantageously be obtained with a single measurement by the device. With one measurement, for example, all necessary physiological data relating to the eye in question, such as sphere, cylinder, axis, refractive power of the cornea or the entire eye, can be determined. It is therefore no longer necessary to carry out two consecutive measurements, with an autorefractometer and a topography system, on one eye. This further speeds up the selection process and any falsification of the measuring results by a change in the measuring conditions can be ruled out.

Obtaining measuring data from corneal central radii of a cornea can also be envisaged. This measurement can preferably be carried out with the keratometer.

It is particularly advantageous if measuring data of a corneal diameter of a cornea is obtained. A so-called "white to white" measurement covers a measurement of the cornea diameter, which is essentially determined by an external diameter of an iris. Measurement of the cornea diameter is particularly important for the selection of soft contact lenses or their diameter as well as for checking the contact lens position on the cornea.

Measuring data relating to the cornea over and beyond the cornea diameter can also be obtained. This means that not only are central radii of the cornea in the area of the iris determined, but also bending radii or a corneal topography in the areas of the cornea extending beyond the iris. Accordingly, the keratometer can be designed in such a way that the entire cornea is measured and/or corresponding topography data obtained.

The measuring method can also be used to determine keratoconus of a cornea and to obtain the measurements thereof. As a keratoconus is not generally formed centrally on the cornea, its determination by means of a topography system designed solely to obtain measurements in order to select a contact lens is either not possible or only possible to a limited extent. For example, by using a keratometer with a single annular source of illumination a keratoconus already formed on a cornea can be detected. Detecting a keratoconus can, amongst other things, lead to the selection of hard contact lenses, for example, as these can beneficially flatten the keratoconus.

By means of the opthalmological device a cross-section of the eye can also be obtained, whereby the image data from the cross-section can be used in calculating the contact lens data. With the aid of the cross-section image the thickness of the cornea as well as the bending radii of a cornea can also be determined. Furthermore, a cross-section image, which can be produced by means of an imaging apparatus comprising slit lighting and a camera in a Scheimpflug arrangement, is particularly suitable for measuring a keratoconus and a reduced cornea thickness in this area.

The database can advantageously contain contact lens data and contact lens adaptation regulations of different contact lens manufacturers. It is therefore possible to select a particularly well-fitting contact lens for a patient.

Also during a selection, material data of contact lenses can be taken into consideration and/or contained in the database. In addition to the aforementioned data, other data relating to soft contact lenses, such as, for example, air permeability of the contact lens material and other material data can be taken into account.

It is of particular advantage if information on the availability of the proposed contact lens is issued. Contact lenses are available in various sizes and/or visual acuity stages. Any details of stocks and delivery times of the contact lenses in question can also form part of the selection of a contact lens. Thus, in addition to the most suitable contact lens from physiological points of view, a selection decision can also be made on the basis of its availability.

Accordingly it is advantageous if the database can be coordinated with an device-external database. The data can for example be preconfigured on a PC and transferred to the opthalmological device. In this way it is possible to take into account the current range of contact lenses. Transfer can take place via WLAN. But it is also conceivable to set up a direct connection to the manufacturers' databases from the device itself via the internet.

In the opthalmological device according to the invention for implementing the method according to the invention, the keratometer, the autorefractometer and means of dataprocessing are arranged in a joint housing of the opthalmological device.

In this way it is no longer necessary to connect several devices to each other.

Thus, in accordance with a first method embodiment of the present invention, a method of determining and selecting a contact lens with an opthalmological device for examining the eyes, wherein the opthalmological device comprises a keratometer and an autorefractometer as well as means of dataprocessing, whereby a refractive power of an eye and a topography of a cornea are determined, whereby refraction data describing a refraction of an eye to be examined are obtained, whereby topographic data describing the topography of the cornea of the eye are obtained, wherein the method includes the steps of: calculating, on the basis of the obtained refraction and topography data contact lens data, and selecting a contact lens from a database of the device.

Further advantageous forms of embodiment of an opthalmological device are set out in the descriptions of feature in additional method embodiments. For example, in accordance with a second method embodiment of the invention, the first method embodiment is modified so that a comparison of the calculated contact lens data with the contact lens data contained in the data base is carried out. In accordance with a third method embodiment of the invention, the first method embodiment or the second method embodiment are further modified so that the measuring data, the calculated contact lens data and the contact lens data of the selected contact lens are outputted. In accordance with a fourth method embodiment of the present invention, the first method embodiment, the second method embodiment and the third method embodiment, are further modified so that several calculations in various calculation modes are carried out.

In accordance with a fifth method embodiment of the present invention, the first method embodiment, the second method embodiment, the third method embodiment, and the fourth method embodiment, are further modified so that contact lens adaptation regulations are taken into account in a selection. In accordance with a sixth method embodiment of the present invention, the first method embodiment, the second method embodiment, the third method embodiment, the fourth method embodiment, and the fifth method embodiment, are further modified so that the measuring data are obtained with a single measurement by the device.

In accordance with a seventh method embodiment of the present invention, the first method embodiment, the second method embodiment, the third method embodiment, the fourth method embodiment, the fifth method embodiment, and the sixth method embodiment, are further modified so that measurements of corneal central radii of the cornea are obtained. In accordance with an eighth method embodiment of the present invention, the first method embodiment, the second method embodiment, the third method embodiment, the fourth method embodiment, the fifth method embodiment, the sixth method embodiment, and the seventh method embodiment, are further modified so that measurements of the corneal thickness of the cornea are obtained. In accordance with a ninth method embodiment of the present invention, the eight method embodiment is further modified so that measurements of the cornea going beyond the cornea diameter are obtained. In accordance with a tenth method embodiment of the present invention, the first method embodiment, the second method embodiment, the third method embodiment, the fourth method embodiment, the fifth method embodiment, the sixth method embodiment, the seventh method embodiment, the eighth method embodiment, and the ninth method embodiment, are further modified so that a keratoconus of the cornea is determined and measurements thereof obtained.

In accordance with an eleventh method embodiment of the present invention, the first method embodiment, the second method embodiment, the third method embodiment, the fourth method embodiment, the fifth method embodiment, the sixth method embodiment, the seventh method embodiment, the eighth method embodiment, the ninth method embodiment, and the tenth method embodiment, are further modified so that a cross-section of an eye is obtained and the corresponding image data are used in the calculation. In accordance with a twelfth method embodiment of the present invention, the first method embodiment, the second method embodiment, the third method embodiment, the fourth method embodiment, the fifth method embodiment, the sixth method embodiment, the seventh method embodiment, the eighth method embodiment, the ninth method embodiment, the tenth method embodiment, and the eleventh method embodiment, are further modified so that the database covers contact lens data and contact lens adaptation regulations of various contact lens manufacturers. In accordance with a thirteenth method embodiment of the invention, the first method embodiment, the second method embodiment, the third method embodiment, the fourth method embodiment, the fifth method embodiment, the sixth method embodiment, the seventh method embodiment, the eighth method embodiment, the ninth method embodiment, the tenth method embodiment, the eleventh method embodiment, and the twelfth method embodiment, are further modified so that material data of contact lenses are taken into account.

In accordance with a fourteenth method embodiment of the present invention, the first method embodiment, the second method embodiment, the third method embodiment, the fourth method embodiment, the fifth method embodiment, the sixth method embodiment, the seventh method embodiment, the eighth method embodiment, the ninth method embodiment, the tenth method embodiment, the eleventh method embodiment, the twelfth method embodiment, and the thirteenth method embodiment, are further modified so that information relating to the availability of the proposed contact lens is issued. In accordance with a fifteenth method embodiment of the invention, the first method embodiment, the second method embodiment, the third method embodiment, the fourth method embodiment, the fifth method embodiment, the sixth method embodiment, the seventh method embodiment, the eighth method embodiment, the ninth method embodiment, the tenth method embodiment, the eleventh method embodiment, the twelfth method embodiment, the thirteenth method embodiment, and the fourteenth method embodiment, are further modified so that the database is coordinated with a device-external database.

In accordance with a first apparatus embodiment of the present invention, an opthalmological device for implementing the method in according with the first method embodiment, the second method embodiment, the third method embodiment, the fourth method embodiment, the fifth method embodiment, the sixth method embodiment, the seventh method embodiment, the eighth method embodiment, the ninth method embodiment, the tenth method embodiment, the eleventh method embodiment, the twelfth method embodiment, the thirteenth method embodiment, the fourteenth method embodiment, or the fifteenth method embodiment, is provided, wherein the opthalmological device is characterised in that a keratometer, an autorefractometer and means of dataprocessing are arranged in a joint housing of the opthalmological device.

BRIEF DESCRIPTION OF THE DRAWINGS

The invention will be described below with reference to the attached FIG. 1, which illustrates print-out showing determined measurements and selected contact lens.

DETAILED DESCRIPTION OF THE INVENTION

Figure 2:
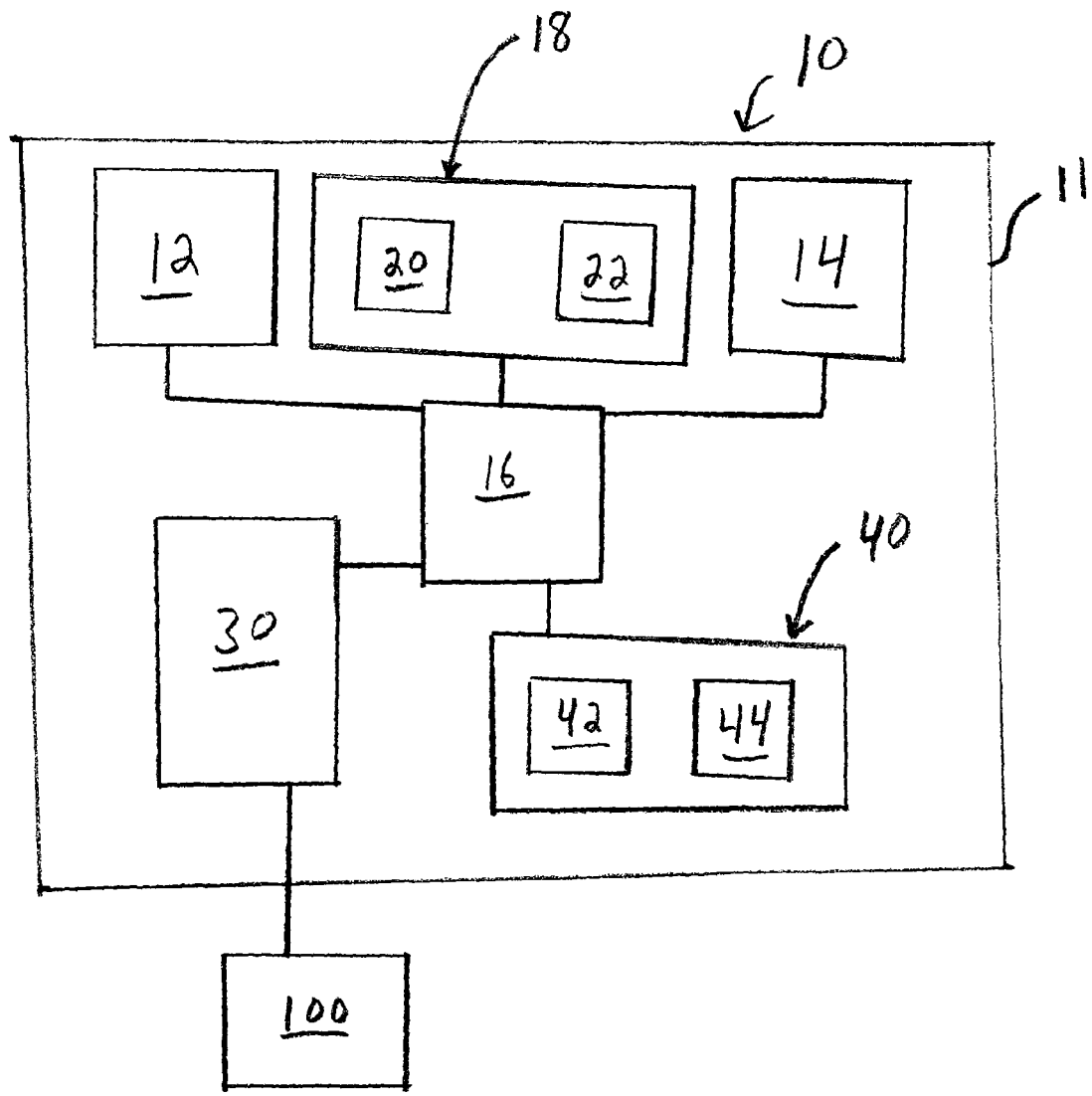
FIG. 2 is a schematic drawing showing an opthalmological device in accordance with the present invention that carries out the method embodiment(s) of the invention.

As described above in the summary of the invention, the determined measurements and selected contact lens are the product of a method of determining and selecting a contact lens using an opthalmological device for examining the eyes, wherein the opthalmological device includes a keratometer and an autorefractometer as well as means of dataprocessing, whereby the refractive power of an eye and the topography of a cornea are determined using the autorefractometer and the keratometer, respectively, whereby refraction data describing the refraction of the eye to be examined are obtained using the autorefractometer, whereby topographic data describing the topography of the cornea of the eye are obtained using the keratometer, wherein the method includes the steps of: (a) calculating, on the basis of the obtained refraction and topography data contact lens data, and (b) selecting a contact lens from a database of the opthalmological device. In accordance with the present invention, the means of dataprocessing (i.e., a data processor) performs the calculation of step (a) and selects the contact lens from the database of the opthalmological device in step (b).

The general method, of course, may be modified to include carrying out a comparison of the calculated contact lens data with the contact lens data contained in the database, such as may be carried out by the data processing means. The method may further include outputting the measuring data (i.e., the measured data), the calculated contact lens data and the contact lens data of the selected contact lens (See, e.g., FIG. 1). Thus, the opthalmological device may include an output apparatus for printing out as output the measured data, the calculated contact lens data, and the contact lens data of the selected contact lens. The method may also include carrying out several calculations in various calculation modes, carried out of course by the data processing means.

Furthermore, the general method described above may be modified so that contact lens adaptation regulations are taken into account in selection of the contact lens from the database of the opthalmological device. The general method may also be modified so that the measuring data are obtained with a single measurement by the opthalmological device using, for example, the keratometer and the autorefractometer of the opthalmological device. The general method may also be modified so that measurements of corneal central radii of the cornea are obtained using the keratometer of the opthalmological device. The general method may also be modified so that measurements of the corneal thickness of the cornea are obtained using the keratometer of the opthalmological device. The opthalmological device may also be used to obtain measurements of the cornea going beyond the cornea diameter using the keratometer of the opthalmological device. The general method may also be modified so that a keratoconus of the cornea is determined and measurements thereof are obtained using the keratometer of the opthalmological device. Of course, the general method may also be modified so as to obtain a cross-section of an eye and the corresponding image data using an imaging apparatus of the opthalmological device, wherein the cross-section of the eye and corresponding image data are used in the calculation of step (a).

The general method, in accordance with the present invention, may also be modified so that the database of the opthalmological device includes contact lens data and contact lens adaptation regulations of various contact lens manufacturers. Thus, the general method of the invention may be modified so that it takes into account material data of contact lenses. The general method of the invention may also be modified so that information relating to the availability of the proposed contact lens is issued. Furthermore, the general method of the invention may be modified so that the database of the opthalmological device is coordinated with a device-external database.

The determined measurements and selected contact lens can be shown, for example, in the form of a print-out, as shown in FIG. 1, issued by the opthalmological device itself. As can be seen from the example, in addition to the objective measurements, the details of a necessary contact lens are shown, on the basis of which a contact lens is selected from a database. In relation to the selected contact lens, further information on the available refractive power graduations and the calculated contact lens diameter is issued.

Having described in detail, various method embodiments in accordance with the present invention, an opthalmological device 10 for implementing the method in according with the present invention is described as follows, and as shown in FIG. 2. The opthalmological device 10 includes a keratometer 12, an autorefractometer 14 and means of dataprocessing 16 arranged in a joint housing 11 of the opthalmological device. The keratometer 12 and the autorefractometer 14 are operably connected to send data to the data processing means 16 (i.e., a data processor). An imaging apparatus 18 comprising slit lighting 20 and a camera 22 may also be included in the opthalmological device 10, and the imaging apparatus is operably connected to send cross-section image data to the data processing means 16.

The opthalmological device is also provided with a database 30 operably connected to the data processing means 16, which may retrieve information stored in the database 30. Information stored in the database 30 may include contact lens data, contact lens adaptation regulations, adaptation regulations for contact lens of various manufacturers, data relating to soft contact lenses, such as, for example, air permeability of the contact lens material and other material data, details of stocks and delivery times of the contact lenses (i.e., availability of contact lenses), etc. The database 30 may be connected with an external database 100, and may receive information from the external database 100.

The opthalmological device 10 may also be provided with an output apparatus 40, such as may include a display screen 42 for displaying the contact lens data of the selected contact lens, and a print-out device 44 (i.e., a printer) for printing-out the contact lens data of the selected contact lens (See, e.g., print-out of FIG. 1)

The invention claimed is:

1. A method of determining and selecting a contact lens using an opthalmological device for examining eyes, wherein the opthalmological device comprises a keratometer and an autorefractometer as well as data processing means, whereby a refractive power of an eye and a topography of a cornea of the eye are determined using the autorefractometer and the keratometer, respectively, so that refraction data describing the refraction of the eye examined are obtained by the autorefractometer, and whereby topographic data describing the topography of the cornea of the eye are obtained by the keratometer, wherein the method comprises the steps of:
   (a) using the data processing means to calculate contact lens data on the basis of the refraction data and the topographic data obtained by the autorefractometer and the keratometer, respectively; and
   (b) selecting a contact lens from a database of the opthalmological device based on the calculated contact lens data.

2. The method according to claim 1, further comprising the step of:
   (c) carrying out a comparison of the calculated contact lens data with contact lens data contained in the database of the opthalmological device.

3. The method according to claim 1, further comprising the step of:
   (c) outputting measured data, the calculated contact lens data and contact lens data of the selected contact lens using an output apparatus of the ophthalmologic device.

4. The method according to claim 1, wherein the step (a) involves carrying out several calculations in various calculation modes.

5. The method according to claim 1, wherein the selection of the contact lens from the database takes into account contact lens adaptation regulations.

6. The method according to claim 3, wherein the measured data are obtained with a single measurement conducted by the opthalmological device.

7. The method according to claim 1, wherein the topographic data includes measurements of corneal central radii of the cornea of the eye obtained by the keratometer.

8. The method according to claim 1, wherein a keratoconus of the cornea of the eye is determined and measurements thereof are obtained using the keratometer of the ophthalmologic device.

9. The method according to claim 1, wherein the method further includes the step of:
   obtaining a cross-section of the eye and corresponding image data using an imaging apparatus of the ophthalmologic device, wherein data corresponding to the cross-section of the eye and corresponding image data are used in the calculation of the calculated contact lens data.

10. The method according to claim 1, wherein the database of the ophthalmologic device includes first contact lens data and contact lens adaptation regulations of various contact lens manufacturers.

11. The method according to claim 1, wherein material data of contact lenses are taken into account when selecting the contact lens from the database of the ophthalmologic device.

12. The method according to claim 1, wherein information relating to the availability of the selected contact lens is issued.

13. The method according to claim 1, wherein the database of the ophthalmologic device is coordinated with a device-external database.

14. An opthalmological device operable to implement the method according to claim 1, wherein the opthalmological device comprises:
   (A) a keratometer;
   (B) an autorefractometer; and
   (C) dataprocessing means, wherein the keratometer, the autorefractometer, and the dataprocessing means are arranged in a joint housing of the opthalmological device.

15. A method of determining and selecting a contact lens using an opthalmological device for examining eyes, wherein the opthalmological device comprises a keratometer and an autorefractometer as well as data processing means, whereby a refractive power of an eye and a topography of a cornea of the eye are determined using the autorefractometer and the keratometer, respectively, so that refraction data describing the refraction of the eye examined are obtained by the autorefractometer, and whereby topographic data describing the topography of the cornea and the measurements of the corneal diameter of the cornea of the eye are obtained by the keratometer, wherein the method comprises the steps of:
   (a) using the data processing means to calculate contact lens data on the basis of the refraction data and the topographic data obtained by the autorefractometer and the keratometer, respectively; and
   (b) selecting a contact lens from a database of the opthalmological device based on the calculated contact lens data.

16. The method according to claim 15, wherein the topographic data includes measurements of the cornea going beyond the cornea diameter as obtained by the keratometer.

* * * * *

UNITED STATES PATENT AND TRADEMARK OFFICE
CERTIFICATE OF CORRECTION

PATENT NO. : 8,220,927 B2  
APPLICATION NO. : 12/792255  
DATED : July 17, 2012  
INVENTOR(S) : Andreas Steinmuller Page 1 of 1

It is certified that error appears in the above-identified patent and that said Letters Patent is hereby corrected as shown below:

ON THE TITLE PAGE:

Item (73) Assignee: in Line 2 should read:
Wetzlar-Dutenhofen (DE)

Signed and Sealed this  
Sixth Day of November, 2012

David J. Kappos  
*Director of the United States Patent and Trademark Office*